United States Patent [19]
Browne

[11] Patent Number: 5,118,627
[45] Date of Patent: Jun. 2, 1992

[54] PAPOVA VIRUS CONSTRUCTION

[75] Inventor: Jeffrey K. Browne, Camarillo, Calif.

[73] Assignee: Amgen, Thousand Oaks, Calif.

[21] Appl. No.: 584,132

[22] Filed: Feb. 27, 1984

[51] Int. Cl.$^5$ ................. C12N 15/00; C12N 15/33
[52] U.S. Cl. ..................... 435/172.3; 435/69.3; 435/320.1
[58] Field of Search ............... 435/317, 172.3, 68, 435/91, 235, 236, 240, 948; 935/22, 23, 27, 32, 34, 36, 40, 56, 57, 69, 70, 72, 29, 52; 536/27

[56] References Cited

U.S. PATENT DOCUMENTS

| | | | |
|---|---|---|---|
| 4,403,035 | 9/1983 | Anderson et al. | 435/172.3 |
| 4,419,446 | 12/1983 | Howley et al. | 435/317 |
| 4,442,205 | 4/1984 | Hamer et al. | 435/317 |
| 4,446,235 | 5/1984 | Seeburg | 935/32 |

FOREIGN PATENT DOCUMENTS

| | | | |
|---|---|---|---|
| 0037723 | 10/1981 | European Pat. Off. | 935/70 |
| 0062574 | 10/1982 | European Pat. Off. | 935/70 |
| 0101617 | 2/1984 | European Pat. Off. | 935/70 |
| 2105344 | 3/1983 | United Kingdom | 435/172.3 |

*Primary Examiner*—Christine Nucker
*Assistant Examiner*—T. Cunningham
*Attorney, Agent, or Firm*—Marshall, O'Toole, Gerstein, Murray & Bicknell

[57] ABSTRACT

A microbial shuttle vector is disclosed which is independently replicative in bacterial cells and mammalian cells and includes in its DNA sequence bacterial plasmid sequences allowing selection and replication in bacterial cells, an SV40 viral origin of replication, and either an SV40 functional "early gene" promoter and functional "early gene" terminator or an SV40 functional "late gene" promoter and functional "late gene" terminator, the vector having a unique restriction endonuclease enzyme recognition site between the promoter and terminator for insertion of an exogenous gene. The presence of restriction endonuclease enzyme recognition sites facilitative of insertion of a viral functional "late gene" into the "early gene" promoter/terminator vector in a single step allows for conversion of the shuttle vector into a lytic vector of an exogenous gene. The presence of restriction endonuclease enzyme recognition sites facilitative of insertion of a viral functional "late gene" into the "late gene" promoter/terminator vector in a single step allows for conversion of the shuttle vector into a lytic vector.

20 Claims, No Drawings

PAPOVA VIRUS CONSTRUCTION

BACKGROUND

The present invention relates generally to the manipulation of genetic materials and more particularly to methods and materials for securing expression of exogenous, viral-vector-borne genes in mammalian cells.

Expression of exogenous genes has been attempted by employing a variety of host cell systems including bacterial cell, yeast cell and mammalian cell systems. Mammalian cell systems for exogenous gene expression have displayed distinct advantages when compared with both bacterial and yeast systems. In the lower organism cell systems, incomplete post-translational processing (i.e., glycosylation or proteolysis) of the exogenous gene may occur, resulting in loss of significant antigenic determinants and/or biological activity of the polypeptide coded for by the exogenous gene. By contrast, mammalian host cells provide the factors necessary for proper processing, proper secondary or tertiary structure and excretion or inclusion into the cell membrane. See, Berman, P., et al., *Science*, 222, 524-527 (1983).

A common protocol for expression of exogenous genes by mammalian cells maintained in culture is through infection of cells with viral vectors carrying exogenous gene DNA sequences. Typically, the exogenous gene is placed under the influence of viral controlling elements as a replacement for a deleted viral gene. A complementing, co-infecting helper virus is required to ensure propagation of the recombinant genome in the infected host cells by supplying the proteins ordinarily expressed by the deleted viral gene. As one example, SV40, a DNA tumor virus of the Papova virus group, which normally infects monkey kidney cells, has been employed extensively as a eukaryotic expression vector in this manner.

Another commonly-employed method for obtaining expression of exogenous genes in mammalian cells is through the introduction into the cells of shuttle vectors carrying the exogenous gene of choice. Shuttle vectors contain both bacterial plasmid sequences and viral DNA sequence, the former sequences allowing selection and replication in bacteria and the latter permitting expression and/or replication in mammalian cell culture. Therefore, like bacterial or yeast vectors, all manipulations involving the insertion of an exogenous gene and propagation of these vectors can be conveniently accomplished in *E.coli* prior to expression of the exogenous gene in mammalian cells. As one example, the above-described SV40 viral DNA has also been extensively employed in shuttle vector constructions.

An SV40-based viral vector may be constructed by replacing SV40 early gene regions or SV40 late gene regions with an exogenous gene sequence. If an exogenous gene is inserted to replace a deleted early viral gene DNA sequence coding for T antigen, the recombinant virus must be propagated in the presence of SV40 T antigen, e.g., supplied by simian COS-1 cells (ATCC CRL1650) or co-infection with a helper virus. Alternatively, if late viral gene DNA is excised from SV40 to permit insertion of the exogenous gene coding sequence, the early T antigen gene is present but the DNA sequences coding for expression of essential capsid proteins is absent. Therefore, these recombinant viruses must infect a host cell in concert with a "helper" virus which supplies the missing proteins. Early gene replacement viral vectors, which are easily propagated in COS cells which supply SV40 T antigen, are technically more adaptable to experimental manipulation than late gene replacement viral vectors, which require co-infection with a helper virus.

A disadvantage incurred in using the SV40 viral vectors for expression of exogenous genes in mammalian cells, resides in inherent limitations on the size of the viral vector. It has been concluded that the icosohedral symmetry of the SV40 virion imposes restrictions on the size of the DNA that could be encapsulated by its capsid proteins. Because the expression of the exogenous gene typically requires propagation of the recombinant molecules, the addition of exogenous genes without removal of viral sequences, or the insertion of genes larger than the viral sequences removed is precluded by the packaging constraints of SV40 [see, Liu, C., et al., "Expression of HE Surface Antigen Using Lytic and Non-Lytic SV40 Based Vectors in Eukaryotic Viral Vectors", Y. Gluzman, ed., Cold Spring Harbor Laboratory, Cold Spring, N.Y., 1982, pages 55-60; and Liu, et al., DNA, 1, pages 213-221 (1982)].

In Liu, DNA, 1, supra, an SV40 vector for the direct expression of exogenous genes was constructed by eliminating SV40 genome sequences between HindIII (1493) [6 nucleotides 5' to the initiation codon for the gene coding for the major SV40 late protein, VP1, which is essential in capsid formation] and BamHI (2533) [50 nucleotides 5' to the termination codon for that gene]. A unique EcoRI restriction endonuclease enzyme recognition site was introduced into the SV40 genome at the HindIII terminus to allow the SV40 fragment to be cloned into pBR322 and amplified. A BamHI/EcoRI exogenous gene sequence, e.g., HBsAg, is inserted into the SV40 fragment in place of the deleted VP1 sequence and the SV40-HBsAg fragment cloned into a pBR322 derivative and amplified. Cleavage with BamHI and self-ligation results in a recombinant virus plasmid vector, therefore, lacking only the coding region of VP1 and containing the whole protein coding region for T antigen. When the recombinant SV40/hepatitis B virus DNA was introduced into permissive monkey cells by DNA transfection in the presence of helper virus (tsA28), which supplies the capsid protein normally expressed by the deleted VP1, HBsAg was synthesized at a level comparable to that of VP1.

Liu, et al., also indicated that size restrictions exist with regard to the exogenous gene that could be inserted into this SV40 vector, approximately limited to the size of the coding region of VP-1 protein (about 900 base pairs).

SV40 recombinant virus vectors described in Gething, et al., "The Expression of the Influenza Virus Hemaglutinin Gene from SV40-HA Recombinants" in *Eukaryotic Viral Vectors*, Y. Gluzman, ed., Cold Spring Harbor Laboratory, Cold Spring Harbor, N.Y., 1982, pages 29-33; and Gething, M., et al., *Nature*, 293, pages 620-625 (1981), provide for the insertion of an exogenous gene sequence coding for the influenza virus hemaglutinin (HA) gene to replace either the SV40 late or early gene coding regions.

In formation of a late replacement vector, the exogenous influenza virus hemaglutinin gene was inserted between the HpaII (346) and BamHI (2533) sites of the SV40 genome replacing the deleted late gene region. Thereafter, the recombinant viral genome SV40-HA was cloned into the BamHI site of an *E.coli* pBR322 derivative plasmid and propagated in *E.coli*. The recombinant SV40-HA genome was excised from the plasmid by BamHI digestion, purified and self-ligated to form the vector which contained the SV40 origin of DNA replication and an intact set of early genes including an intact copy of the gene coding for SV40 large T antigen. Presence of the early coding region and viral origin of replication permitted replication of the vector DNA in permissive simian cells and complementation by helper virus supplied SV40 capsid proteins for the assembly of infectious virions.

Similarly described in these references is an early replacement vector in which the HA gene was inserted into the SV40 genome between the HindIII (5171) and BamHI (2532) restriction endonuclease enzyme recognition sites. The recombinant viral genome was thereafter cloned, propagated, purified and ligated as described above to yield a vector containing the SV40 origin of DNA replication and an intact set of late genes. Because the vector lacked the early gene coding for large T antigen, it could not replicate in simian cells unless functional T antigen was supplied by using as a permissive host the COS-1 line of SV40 transformed monkey cells carrying an endogenously expressed copy of the T antigen gene. A low rate of productive infection of the COS-1 cells was observed.

"Shuttle vectors" are hybrid vectors containing bacterial plasmid sequences and portions of SV40 gene sequences allowing selection and replication in bacteria and transient expression and/or replication in mammalian cells. As a class, shuttle vectors cannot be maintained in mammalian cells where expression of an exogenous gene insert is lost after a few days. The shuttle vectors disclosed in Southern, et al., "Mammalian Cell Transformation with SV40 Hybrid Plasmid Vectors", in *Eukaryotic Viral Vectors*, Y. Gluzman, ed., Cold Spring Harbor Laboratory, Cold Spring Harbor, N.Y. (1982), pages 41–45 include sequences from *E.coli* pBR322 that permit selection and propagation in *E.coli* and segments of the SV40 viral genome that constitute a defined eukaryotic transcription unit-promoter, coding region and polyadenylation site. The phosphotransferase gene from TN5 (neo) was subcloned into pBR322 and subsequently inserted into the pSV family of plasmid vectors. The resulting pSV-neo hybrid plasmids contained the pBR322 origin of DNA replication and the beta-lactamase selective marker gene, the neo gene segment from TN5, the SV40 origin of DNA replication, the SV40 early promoter, 5' to the neo gene, the SV40 DNA sequence of unspecified size at the 3' side of the neo gene including the small t antigen intervening sequence, and the SV40 early region polyadenylation signal. These plasmids also contain the entire T antigen coding region, resulting in a rather large vector, which cannot be converted to a lytic viral vector by simple deletion of the pBR322 DNA sequence. Further, these vectors could not be readily manipulated to allow replacement of the neo gene by a different gene of interest.

SV40 recombinant early replacement viral vectors have most recently been employed to express portions of the HBsAg according to a construction described by Laub, O., et al., *J.Virol.*, 48, 271–280 (1983). The SV40-HBsAg recombinants were constructed by inserting the SV40 genome into the BamHI site of pBR322 for amplification. Partial digestion of the SV40 sequence with HindIII and thereafter BclI, allowed deletion of the early gene sequence between HindIII (5171) [8 nucleotides 5' to the translation initiation codon of the large T antigen gene] and BclI (2770) [77 nucleotides 5' to the termination codon of the large T antigen], resulting in recombinant pLSV. The exogenous HBsAg coding sequence was inserted into the pLSV recombinant genome as a TacI/BamHI fragment (and alternatively a AvaI blunt ended/BamHI fragment) for amplification in *E.coli*. Thereafter, digestion with BamHI removed the pBR322 portion of the recombinant and self-ligation resulted in plasmids containing an SV40 origin of replication, a functional set of SV40 late genes, HBsAG replacing the SV40 early genes, the SV40 early promoter sequence and polyadenylation site. Transfection of the vectors into COS cells which supply T antigen permitted propagation of the virus.

There has yet to be disclosed to the art an easily alterable intermediate SV40 recombinant shuttle vector which would allow ready insertion and replacement of a desired exogenous gene between an SV40 promoter and terminator in the same vector for expression in mammalian cells. The above-described SV40 recombinant vectors have intrinsic limitations on their use in mammalian cell systems for expression of exogenous genes, because for each desired exogenous gene, a new SV40 vector must be constructed. The absence of unique restriction endonuclease enzyme recognition sites both behind the SV40 early promoter and near the terminator prevents easy insertion of exogenous genes and requires the alteration of termini in both the SV40 genomes and the exogenous gene fragments as illustrated by the above-described prior art manipulations.

Further, evaluation of the efficacy of lytic early or late gene replacement viral vectors, which propagate as viruses when grown in COS cells or with a helper virus is procedurally complex and time-consuming in contrast to the rapid evaluation of a given vector construction permitted by use of shuttle vectors. Maintained in bacteria, shuttle vectors will transiently express an exogenous gene insert for several days upon introduction into mammalian cells. For the production of an exogenous gene product in large quantities, however, lytic viral vectors are considerably more efficient than shuttle vectors.

There exists, therefore, a need in the art for shuttle vectors which can be readily manipulated to express any desired exogenous gene by replacement of SV40 sequences under the control of SV40 promoters and terminators, and allows for the conversion of the shuttle vector into a lytic viral vector.

BRIEF SUMMARY

As one aspect of the present invention, a microbial shuttle vector is described which is independently replicative in bacterial cells such as *E.coli* and mammalian cells such as monkey COS cells. The vector DNA sequence codes for an SV40 viral origin of replication, an SV40 functional early gene promoter and an SV40 functional early gene terminator, and has a unique restriction endonuclease enzyme recognition site for insertion of an exogenous gene between the promoter and terminator. The vector also possesses restriction endonuclease enzyme recognition sites facilitative of insertion of a functional late SV40 gene region into the DNA sequence in a single step. Any selected exogenous gene having a maximum length of approximately 2300 base pairs may be employed in the vector e.g., hepatitis B surface antigen (HBsAg), for insertion at the unique restriction endonuclease enzyme recognition site, preferably SalI.

As another aspect of the present invention, another microbial shuttle vector is described which is independently replicative in bacterial cells such as *E.coli* and mammalian cells such as monkey COS cells. The vector DNA sequence codes for an SV40 viral origin of replication, an SV40 functional late gene promoter and an SV40 functional late gene terminator, and has a unique restriction endonuclease enzyme recognition site for insertion of an exogenous gene between the promoter and terminator. The vector also possesses restriction endonuclease enzyme recognition sites facilitative of insertion of a functional early SV40 gene region into the DNA sequence in a single step. Any selected exogenous gene having a maximum length of approximately 2300 base pairs may be employed in the vector e.g., HBsAg, for insertion at the unique restriction endonuclease enzyme recognition site, preferably BamHI.

As yet another aspect of the present invention, there is provided a method for converting an "early gene" microbial shuttle vector to a lytic vector. The method employs the following steps:

(1) forming a microbial shuttle vector independently replicative in bacterial and mammalian cells, said vector comprising a DNA sequence coding for bacterial plasmid sequences allowing replication and selection in bacterial cells, an SV40 viral origin of replication, an SV40 functional early gene promoter and an SV40 functional early gene terminator, an exogenous gene inserted between said promoter and terminator at the position of a unique restriction endonuclease enzyme recognition site, and restriction endonuclease enzyme recognition sites facilitative of insertion of a functional SV40 late gene region in a single step;

(2) inserting the vector containing an exogenous gene into mammalian cells to verify expression of the exogenous gene; and (3) inserting a portion of the SV40 genome into the shuttle vector, thereby converting it to a lytic virus vector having the exogenous gene under control of the promoter, the lytic vector capable of replication and infective viral particle formation in cells supplying SV40 early gene products.

As a further aspect of the present invention, there is provided a method for converting a "late gene" microbial shuttle vector to a lytic vector. The method employs the following steps:

(1) forming a microbial shuttle vector independently replicative in bacterial and mammalian cells, said vector comprising a DNA sequence coding for bacterial plasmid sequences allowing replication and selection in bacterial cells, an SV40 viral origin of replication, an SV40 functional late gene promoter and an SV40 functional late gene terminator, an exogenous gene inserted between said promoter and terminator at the position of a unique restriction endonuclease enzyme recognition site, and restriction endonuclease enzyme recognition sites facilitative of insertion of a functional SV40 early gene region in a single step;

(2) inserting the vector containing an exogenous gene into mammalian cells to verify expression of the exogenous gene; and (3) inserting a portion of the SV40 genome into the shuttle vector, thereby converting it to a lytic virus vector having the exogenous gene under control of the promoter, the lytic vector capable of replication and infective viral particle formation in cells supplying SV40 late gene products.

In practice of the invention to convert either shuttle vector to a lytic vector, the methods may utilize any desired exogenous gene of length up to approximately 2300 base pairs, including, for example, a hepatitis B surface antigen gene. Further, the methods may be employed using monkey COS cells to verify expression and to supply viral T antigen, where needed.

Other aspects and advantages of the present invention will be apparent upon consideration of the following detailed description thereof.

DETAILED DESCRIPTION

The novel products and processes of the present invention are described in the following examples which relate to manipulations involved in constructing SV40 hybrid shuttle/lytic virus vectors to express the exogenous gene for hepatitis B surface antigen (HBsAg).

The following example relates to the construction of an SV40 shuttle vector which can be manipulated for the insertion of a selected exogenous gene.

EXAMPLE 1

Three intermediate plasmids were employed to enable the assembly of an SV40 "early gene promoter" vector for insertion of a selected exogenous gene: pSV08, pSV4S and I3.

An *E.coli* pBR322 derivative, pSV08, obtained from Dr. R. Tjian at University of California, Berkeley, has the following features. 1918 base pairs of the pBR322 sequence from the nucleotide commonly given reference number 2448 through nucleotide numbered 4362 containing the pBR322 origin of replication and ampicillin resistance gene DNA sequences; and having the sticky end of an EcoRI restriction endonuclease enzyme recognition site at the terminus adjacent nucleotide 4362 was structurally modified by the addition of the following HindIII linker immediately adjacent to nucleotide 2448:

5' AAGCTTG-3'.

A second intermediate vector pSV4S was constructed in the following manner. The SV40 virus was digested with restriction endonuclease enzyme PvuII, producing three PvuII/PvuII fragments of differing sizes. One of these fragments contained the sequence (HindIII at position number 5171 to PvuII at position number 270) which codes for the counterclockwise "early gene" promoter and origin of replication of the SV40 virus. An EcoRI linker (Collaborative Research) was added to the 5' and 3' termini of each of the three fragments, thereby forming three EcoRI/EcoRI fragments of differing sizes. These fragments were digested with HindIII and the 340 base pair HindIII/EcoRI fragment was isolated by polyacrylamide gel electrophoresis.

The 1918 base pair EcoRI/HindIII fragment, pSV08, was ligated to the 340 base pair EcoRI/HindIII fragment from the SV40 genome, forming plasmid pSV4. Plasmid pSV4 was digested with HindIII, the HindIII sticky end converted to a blunt end by treatment with Klenow, and a SalI restriction endonuclease enzyme recognition site added thereon by a linker (Collaborative Research). Religation at the SalI site formed plasmid pSV4S.

To construct yet another intermediate vector containing the terminator sequence of the early SV40 genes, the complete SV40 genome was digested with BclI, which cut at SV40 nucleotide number 2770. The BclI sticky end was blunt-ended with Klenow and converted into a SalI recognition site by the attachment of a SalI linker (Collaborative Research). This unligated BclI/SalI SV40 sequence was thereafter digested with HindIII, and the 1062 base pair SalI/HindIII fragment isolated by agarose gel electrophoresis. This SalI/HindIII SV40 fragment was inserted into the large fragment of SalI/HindIII digested pBR322, resulting in plasmid I3.

An SV40 vector for insertion of a selected exogenous gene was thereafter assembled by employing fragments of the above-described plasmids, pSV08, pSV4S and I3, in the following procedures. pBR322-derived pSV08 was cleaved with HindIII and PvuI, and the large fragment was isolated for ligation with the small fragment containing the SV40 origin of replication and "early gene" promoter resulting from cleavage of pSV4S with PvuI and SalI. Plasmid I3 was then digested with HindIII and SalI and the small fragment containing the sequence coding for the SV40 early gene terminator was isolated and ligated between the SalI site of the pSV4S fragment and the HindIII site of the pSV08 fragment.

Resulting plasmid vector pSV4SET contained a pBR322 sequence, the SV40 origin of replication and "early gene" promoter sequence followed by the SV40 "early gene" terminator sequence. A unique SalI restriction endonuclease enzyme recognition site is located between the terminator and promoter to allow easy insertion of an exogenous gene sequence therebetween.

The following example relates to the construction of another SV40 shuttle vector which can be manipulated to permit the insertion of a selected exogenous gene therein.

EXAMPLE 2

As in Example 1, intermediate plasmids were employed to enable the assembly of an SV40 "late gene promoter" vector for insertion of a selected exogenous gene: pSV010 and pI1.

A first intermediate plasmid, pSV010, obtained from Dr. R. Tjian, at University of California, Berkeley, contains the pBR322 DNA sequence spanning nucleotide numbers 2448 through 4362, with an EcoRI sticky end adjacent nucleotide number 4362, and modified to contain a HindIII linker (Collaborative Research) adjacent nucleotide number 2448, and a segment of the SV40 genome from nucleotide number 5171 to 160. Adjacent to that EcoRI sticky end at nucleotide number 4362 in pSV010 is a polylinker sequence containing the restriction endonuclease enzyme recognition site sequences for EcoRI, HindIII, PstI and BamHI in that order, which sequence bridges the EcoRI site of the pBR322 DNA and the HindIII linker, along with the segment of SV40 DNA.

SV40 DNA was digested with restriction endonuclease enzyme PvuII, producing three PvuII/PvuII fragments of differing sizes. One of these fragments contained the 342 base pair sequence spanning nucleotide number 5171 (HindIII) to nucleotide number 270 (PvuII), which codes for the clockwise "late gene" promoter and origin of replication of the SV40 virus. Synthetic BamHI linkers (Collaborative Research) were ligated to the three PvuII-cut fragments, thereby forming three BamHI/BamHI fragments of differing sizes. These fragments were digested with HindIII and separated by size by agarose gel electrophoresis. The 350 base pair BamHI/HindIII fragment containing the sequence from 517 to 270 was isolated.

pSV010 is thereafter partially cleaved with HindIII and also cleaved with BamHI, and the fragments resulting therefrom are ligated to the 350 base pair SV40 fragment isolated above. Upon transformation into bacteria and screening, the second intermediate plasmid, designated pI1, which contains the large pSV010 fragment including the polylinker, was isolated.

An SV40 vector for insertion of a selected exogenous gene behind the SV40 "late gene" promoter was thereafter assembled by employing fragments of plasmid pI1 and fragments of the SV40 viral genome, according to the following procedures. SV40 DNA was digested with BamHI and BclI endonuclease enzymes, and the 237 base pair fragment spanning SV40 nucleotide numbers 2533 to 2770 and containing the "late gene" viral mRNA polyadenylation signal (i.e., transcription terminator) was isolated by size on polyacrylamide gel electrophoresis. This fragment was ligated to BamHI-digested pI1 in proper orientation vis-a-vis the "late gene" viral promoter therein. The ligation of the BclI sticky end and BamHI sticky end adjacent the polylinker destroyed both recognition sites in the resulting new plasmid pSV3LT.

Resulting plasmid vector pSV3LT contained a pBR322 bacterial sequence, the SV40 origin of replication and "late gene" promoter sequence, followed by the SV40 "late gene" terminator sequence. A unique BamHI restriction endonuclease enzyme recognition site is located between the "late gene" viral promoter and terminator to allow easy insertion of an exogenous gene sequence therebetween.

The following example relates to employing the vector assembled in Example 1 as an SV40 shuttle vector for expression of an exogenous gene.

EXAMPLE 3

Insertion of an exogenous gene into pSV4SET may be easily accomplished by cleavage of the vector at its unique restriction endonuclease enzyme recognition site, SalI, followed by ligation of vector pSV4SET to a SalI fragment containing the exogenous gene. When inserted in proper orientation, the exogenous gene may be placed after the SV40 origin of replication and "early gene" promoter and before the SV40 "early gene" terminator in pSV4SET. The resulting shuttle vector may thereafter be transformed into and propagated in an appropriate bacteria host.

As one example, a hepatitis B surface antigen gene according to the disclosures of co-pending, co-owned U.S. patent application Ser. No. 412,707, filed Aug. 30, 1982 by Grant Bitter, entitled "Expression of Exogenous Polypeptides Including Hepatitis B Surface Antigen in Yeast Cells", the disclosures of which are specifically incorporated by reference herein, was manufactured as a 1371 base pair BamHI fragment which was converted to a SalI fragment by means of SalI linkers (Collaborative Research).

Plasmid pSV4SET was cut with SalI and the HBsAg fragment inserted therein. The resulting shuttle vector, pSV4SET-HBsAg, was transformed into an propagated in E.coli HB101 cells. Vector DNA, isolated from the bacterial host cells, was transformed into mammalian monkey kidney COS-1 cells where the pSV4SET-HBsAg DNA replicated due to the presence of SV40 T antigen in the COS-1 cells and the SV40 origin of replication in the vector. The HBsAg gene product was expressed transiently for 7 to 10 days in an amount of up to 1 μg/ml of culture.

The following example relates to conversion of shuttle vector PSV4SET-HBsAg to a lytic viral vector according to the present invention.

EXAMPLE 4

Once expression of HBsAg is confirmed by transient expression in *E.coli*, pSV4SET-HBsAg may be converted into a lytic viral vector for quantitative production of HBsAg in mammalian cells employing the following procedures.

The entire SV40 viral genome was treated with restriction endonuclease enzymes BglI, which cleaves at nucleotide number 5235, and BamHI, which cleaves at nucleotide number 2533. The fragment containing the late gene region of the SV40 genome spanning nucleotide numbers 235 to 2533 was isolated by agarose gel electrophoresis. This fragment also contains the 5' portion of the SV40 origin of replication and early gene promoter sequence and the 3' portion of the early gene terminator sequence.

pSV4SET-HBsAg was similarly digested with BglI and BamHI, and the fragment containing the HBsAG gene was isolated. This fragment of pSV4SET-HBsAg also contains the 3' portion of the SV40 origin and early promoter and the 5' portion of the early gene terminator, so that when the isolated SV40 BamHI/BglI fragment was ligated to the isolated, similarly digested shuttle vector fragment, the SV40 promoter and terminator sequences were complete.

The resulting lytic viral vector, BSVl, when transfected into monkey kidney COS-1 cells (ATCC CRL1650), expressed the HBsAg gene product at a level of 1 to 10 mg/l of culture medium.

The following example relates to employing the vector assembled in Example 2 as an SV40 shuttle vector for expression of an exogenous gene.

EXAMPLE 5

Insertion of an exogenous gene into pSV3LT may be easily accomplished by cleavage of the vector at its unique restriction endonuclease enzyme recognition site, BamHI, followed by ligation of vector pSV3LT to a BamHI fragment containing the exogenous gene. When inserted in proper orientation, the exogenous gene may be placed after the SV40 origin and "late gene" promoter and before the "late gene" terminator in pSV3LT. The resulting shuttle vector may thereafter be transformed into and propagated in an appropriate bacterial host.

As one example, the hepatitus B surface antigen gene according to the disclosures of co-pending, co-owned U.S. patent application Ser. No. 412,707 and described in Example 3, supra, was manufactured as a 1371 base pair BamHI fragment.

Plasmid pSV3LT was cut with BamHI and the HBsAg-BamHI fragment inserted therein. The resulting shuttle vector, pSV3LT-HBsAg, was transformed into and propagated in *E.coli* HB101 cells. Vector DNA isolated from the bacterial host cells was transformed into mammalian monkey kidney COS-1 cells, where the pSV3LT-HBsAg DNA replicated due to the presence of SV40 T antigen in the COS-1 cells and the SV40 origin of replication in the vector. The HBsAg product was expressed transiently for 7 to 10 days in an amount of approximately 1 μg/ml of culture.

The following example relates to conversion of shuttle vector pSV3LT-HBsAg to a lytic viral vector according to the present invention.

EXAMPLE 6

Once expression of HBsAg is confirmed by transient expression in *E.coli* or monkey COS-1 cells, pSV3LT-HBsAg may be converted into a lytic viral vector for quantitative production of the exogenous gene HBsAg in mammalian cells employing the following procedures.

The entire SV40 viral genome would be treated with restriction endonuclease enzymes BglI, which cleaves at nucleotide number 5235, and BamHI, which cleaves at nucleotide number 2533. The fragment containing the "early gene" region of the SV40 genome, the 5' portion of the SV40 origin of replication and "late gene" promoter sequence, and the "late gene" terminator sequence, would thereafter be isolated.

pSL3VT-HBsAg would then be partially digested with BamHI and completely digested with BglI, and the partial BamHI/BglI fragment containing the HBsAg gene isolated. This fragment of pSV3LT-HBsAg also contains the 3' portion of the SV40 origin and "late gene" promoter so that when the isolated 1435 base pair SV40 "early gene" region fragment was ligated to the isolated shuttle vector fragment, the SV40 promoter and terminator sequences would be complete.

The resulting lytic viral vector, when transfected into monkey kidney COS-1 cells (ATCC CRL1650), would express the HBsAg gene product.

Numerous modifications and variations in the practice of the invention are expected to occur to those skilled in the art upon consideration of the foregoing description of the presently preferred embodiments thereof. As one example, while the examples refer to the use of HBsAg as the exogenous gene, it will be understood that the use of other exogenous genes, i.e., erythropoietin and γ interferon, containing a maximum of approximately 2,300 base pairs is contemplated. Consequently, only such limitations should be placed upon the scope of the invention as appear in the appended claims.

What is claimed is:

1. A shuttle vector replicative in bacterial cells and in mammalian cells supplying SV40 early gene products comprising:

a first DNA segment consisting essentially of an SV40 origin of replication, an SV40 early gene promoter, an SV40 early gene terminator, and a unique restriction site for insertion of an exogenous gene between said promoter and terminator, said promoter being between said unique site and said SV40 origin;

a second DNA segment comprising a restriction site facilitative of insertion of an SV40 late gene region in a single step, said SV40 origin being between said second sequence and said promoter; and a third DNA segment, between said terminator and said second segment, comprising a bacteial origin of replication and a marker selectable in bacterial cells;

the shuttle vector being substantially free of SV40 late gene sequences including SV40 late gene regulatory sequences, SV40 late gene coding sequences and SV40 late gene intervening sequences.

2. The vector according to claim 1 further comprising an exogenous gene encoding hepatitis B surface antigen.

3. The vector according to claim 1 wherein said unique restriction endonuclease enzyme recognition site is a SalI site.

4. The vector according to claim 1 wherein said bacterial cells are *E.coli* cells.

5. The vector according to claim 1 wherein said mammalian cells are monkey COS cells.

6. The vector according to claim 1 wherein said exogenous gene DNA sequence has a maximum length of approximately 2,300 base pairs.

7. A shuttle vector replicative in bacterial cells and in mammalian cells supplying SV40 early gene products comprising:
- a first DNA segment consisting essentially of an SV40 origin of replication, an SV40 late gene promoter, an SV40 late gene terminator and a unique first restriction site for insertion of an exogenous gene between said promoter and terminator, said promoter being between said unique site and said SV40 origin;
- a second DNA segment comprising a restriction site facilitative of insertion of an SV40 early gene region in a single step, said SV40 origin being between said second segment and said promoter; and
- a third DNA segment, between said terminator and said second segment, comprising a bacterial origin of replication and a marker selectable in bacterial cells;
- the shuttle vector being substantially free of SV40 early gene sequences including SV40 early gene regulatory sequences, SV40 early gene coding sequences and SV40 early gene intervening sequences.

8. The vector according to claim 7 further comprising an exogenous gene encoding hepatitis B surface antigen.

9. The vector according to claim 7 wherein said unique restriction endonuclease enzyme recognition site is a BamHI site.

10. The vector according to claim 7 wherein said bacterial cells are *E.coli* cells.

11. The vector according to claim 7 wherein said mammalian cells are cells comprising a helper virus.

12. The vector according to claim 7 wherein said exogenous gene DNA sequence has a maximum length of approximately 2,300 base pairs.

13. A method for constructing a lytic SV40 vector comprising the steps of:
(1) introducing into a mammalian cell a shuttle vector to verify expression of an exogenous gene, said vector comprising: a first DNA segment consisting essentially of an SV40 origin of replication, an SV40 early gene promoter, an SV40 early gene terminator and the exogenous gene inserted between the promoter and terminator, the promoter being between the unique site and the SV40 origin;
a second DNA segment comprising a restriction site facilitative of insertion of an SV40 late gene region in a single step the SV40 origin being between the second segment and the promoter; and
a third DNA segment, between the terminator and the second segment, comprising a bacterial origin of replication and a marker selectable in bacterial cells;
the shuttle vector being substantially free of SV40 late gene sequences including SV40 late gene regulatory sequences, SV40 late gene coding sequences and SV40 late gene intervening sequences;
and
(2) inserting a DNA sequence comprising the SV40 late gene region of the SV40 genome into the shuttle vector, thereby converting it to a lytic vector in cells supplying SV40 early gene products.

14. The method according to claim 13 wherein said exogenous gene encodes hepatitis B surface antigen.

15. The method according to claim 13 wherein said mammalian cells are monkey COS cells.

16. The method according to claim 13 wherein said bacterial cells are *E.coli* cells.

17. A method for constructing a lytic SV40 vector comprising the steps of:
(1) introducing into a mammalian cell a shuttle vector to verify expression of an exogenous gene, said vector comprising: a first DNA segment consisting essentially of an SV40 origin of replication, an SV40 early gene promoter and an SV40 late gene terminator and the exogenous gene inserted between the promoter and terminator;
a second DNA segment comprising a restriction site facilitative of insertion of an SV40 early gene region in a single step; and
a third DNA segment, between the terminator and the second segment, comprising a bacterial origin of replication and a marker selectable in bacterial cells;
the shuttle vector being substantially free of SV40 early gene sequences including SV40 early gene regulatory sequences, SV40 early gene coding sequences and SV40 early gene intervening sequences;
and
(2) inserting a DNA sequence comprising the SV40 early gene region of the SV40 gemone into the shuttle vector, thereby converting it to a lytic vector in cells supplying SV40 late gene products.

18. The method according to claim 17 wherein said exogenous gene encodes hepatitis B surface antigen.

19. The method according to claim 17 wherein said mammalian cells are cells comprising a helper virus.

20. The method according to claim 17 wherein said bacterial cells are *E.coli* cells.

* * * * *